United States Patent
Grey et al.

(10) Patent No.: US 9,433,925 B2
(45) Date of Patent: Sep. 6, 2016

(54) METHOD OF PREPARING EPOXIDATION CATALYSTS

(71) Applicant: Lyondell Chemical Technology, L.P., Houston, TX (US)

(72) Inventors: Roger Grey, West Chester, PA (US); Debra Jackson, Huffman, TX (US); Daniel F. White, Houston, TX (US); Sandor Nagy, Naperville, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 14/602,410

(22) Filed: Jan. 22, 2015

(65) Prior Publication Data

US 2015/0375200 A1    Dec. 31, 2015

Related U.S. Application Data

(60) Provisional application No. 61/930,192, filed on Jan. 22, 2014.

(51) Int. Cl.
*C07D 301/03* (2006.01)
*B01J 21/08* (2006.01)
*B01J 37/08* (2006.01)
*B01J 21/06* (2006.01)
*B01J 35/10* (2006.01)
*B01J 37/02* (2006.01)
*B01J 37/06* (2006.01)
*B01J 29/03* (2006.01)
*B01J 29/89* (2006.01)
*C07D 301/12* (2006.01)
*C07D 301/19* (2006.01)

(52) U.S. Cl.
CPC ............... *B01J 21/08* (2013.01); *B01J 21/06* (2013.01); *B01J 29/0308* (2013.01); *B01J 29/89* (2013.01); *B01J 35/10* (2013.01); *B01J 37/02* (2013.01); *B01J 37/0203* (2013.01); *B01J 37/06* (2013.01); *B01J 37/08* (2013.01); *C07D 301/12* (2013.01); *C07D 301/19* (2013.01); *B01J 2229/32* (2013.01)

(58) Field of Classification Search
CPC .......... C07D 301/19; C07D 301/1219; B01J 21/08; B01J 37/08; B01J 21/06; B01J 29/0308; B01J 29/89; B01J 35/10; B01J 37/02; B01J 37/0203; B01J 37/06
USPC ......................................................... 549/523
See application file for complete search history.

(56) References Cited

U.S. PATENT DOCUMENTS

| | | | |
|---|---|---|---|
| 4,021,454 A | 5/1977 | Wulff et al. | |
| 4,367,342 A | 1/1983 | Wulff et al. | |
| 5,840,650 A * | 11/1998 | Tamura ................ | B01J 21/063 502/240 |
| 6,011,162 A * | 1/2000 | Han ...................... | B01J 21/063 549/529 |
| 6,114,552 A | 9/2000 | Han et al. | |
| 6,383,966 B1 | 5/2002 | Han et al. | |
| 7,713,906 B2 | 5/2010 | Blankenstein et al. | |
| 2003/0166951 A1 | 9/2003 | Blankenstein et al. | |
| 2005/0014960 A1 | 1/2005 | Buijink et al. | |

OTHER PUBLICATIONS

PCT International Search Report and Written Opinion Mailed May 20, 2015 for Corresponding PCT/US2015/012382.

* cited by examiner

*Primary Examiner* — T. Victor Oh

(57) ABSTRACT

A method of preparing epoxidation catalysts is disclosed. The method comprises: (a) adding an inorganic siliceous solid to a column to produce a solid-filled column; (b) adding to the solid-filled column a solution comprising titanium tetrachloride and a hydrocarbon solvent to produce a titanium tetrachloride-impregnated solid; and (c) calcining the titanium tetrachloride-impregnated solid at a temperature from 500° C. to 1000° C. to produce the catalyst. The inorganic siliceous solid has a pore volume of at least 0.8 cm$^3$/g.

16 Claims, No Drawings

METHOD OF PREPARING EPOXIDATION CATALYSTS

CROSS REFERENCE TO RELATED APPLICATIONS

This application claims the priority and benefit of U.S. Provisional Application No. 61/930,192 filed on Jan. 22, 2015, the contents of which are incorporated herein by reference in its entirety.

FIELD

The present disclosure relates to the preparation of a titanium on silica catalyst and to the use of titanated silica catalyst for the epoxidation of olefins to produce an epoxide.

BACKGROUND

Catalysts are important components of many chemical manufacturing processes, and may be used to accelerate the rate of the reaction in question and/or to increase the selectivity or efficiency towards the desired product(s). Catalysts may be utilized in connection with many reactions. In particular, catalysts may be used in the epoxidation of olefins. Improved heterogenous epoxidation catalysts are needed.

SUMMARY

In general, the present disclosure provides a method of preparing a catalyst. The method comprises adding an inorganic siliceous solid to a column to produce a solid-filled column. A solution comprising titanium tetrachloride and a hydrocarbon solvent is added to the solid-filled column to produce a titanium tetrachloride-impregnated solid. The titanium tetrachloride-impregnated solid is calcined at a temperature from 500° C. to 1000° C. to produce the catalyst. The inorganic siliceous solid has a pore volume of at least 0.8 cm$^3$/g.

In some embodiments, the titanium tetrachloride-impregnated solid is washed with additional hydrocarbon solvent prior to calcination.

In some embodiments, the calcined catalyst is washed with a $C_1$-$C_4$ alcohol to produce an alcohol-washed catalyst.

In specific embodiments, the alcohol-washed catalyst is reacted with a silylating agent to produce a silylated catalyst.

In some embodiments, the siliceous solid has a pore volume of at least 2.0 cm$^3$/g.

In some embodiments, the siliceous solid has a surface area from 25 to 1000 m$^2$/g.

In additional embodiments, the siliceous solid is dried at a temperature from 100° C. to 700° C. before or after adding the siliceous solid to the column.

In some embodiments, adiabatic temperature changes that occur are controlled by adjusting the concentration of titanium tetrachloride in the solution, the rate of addition of the solution to the column, or both.

In some embodiments, the catalyst comprises from 0.5 to 10 wt. %, based on the amount of catalyst, of titanium.

In some embodiments, the hydrocarbon solvent is an aromatic hydrocarbon.

The present disclosure also provides a process for forming an epoxide. The process comprises contacting a solution of an olefin and a peroxide with a catalyst to produce the epoxide. The catalyst is made by a method comprising adding an inorganic siliceous solid to a column to produce a solid-filled column, adding to the solid-filled column a solution comprising titanium tetrachloride and a hydrocarbon solvent to produce a titanium tetrachloride-impregnated solid, and calcining the titanium tetrachloride-impregnated solid at a temperature from 500° C. to 1000° C. to produce the catalyst. The inorganic siliceous solid has a pore volume of at least 0.8 cm$^3$/g.

In some embodiments, the olefin is propylene.

In some embodiments, the peroxide is selected from the group consisting of hydrogen peroxide and organic hydroperoxides.

In specific embodiments, the organic hydroperoxide is selected from the group consisting of tert-butylhydroperoxide and ethylbenzene hydroperoxide.

In additional embodiments, the peroxide conversion is at least 50%.

In some embodiments, the peroxide selectivity is greater than 95%.

The present disclosure provides an additional process for forming an epoxide. The process comprises contacting a solution of an olefin and a peroxide with a catalyst to produce the epoxide. The catalyst is made by a method comprising adding an inorganic siliceous solid to a column to produce a solid-filled column, adding to the solid-filled column a solution comprising titanium tetrachloride and a hydrocarbon solvent to produce a titanium tetrachloride-impregnated solid, and calcining the titanium tetrachloride-impregnated solid at a temperature from 500° C. to 1000° C. to produce the catalyst. The inorganic siliceous solid has a pore volume of at least 0.8 cm$^3$/g. The peroxide conversion is within the range of 50 to 99% and the peroxide selectivity is greater than 95%.

In some embodiments, the olefin is propylene.

In some embodiments, the peroxide is selected from the group consisting of hydrogen peroxide and organic hydroperoxides.

In specific embodiments, the organic hydroperoxide is selected from the group consisting of tert-butylhydroperoxide and ethylbenzene hydroperoxide.

The catalyst preparation methods of the present disclosure avoid corrosion issues of handling gas-phase titanium tetrachloride at elevated temperature, permit control over the amount of TiCl$_4$ delivered to the support, and provide unexpectedly better hydroperoxide conversion and epoxide selectivity when compared with catalysts made by solution or incipient wetness methods. The catalyst preparation methods of the present disclosure can utilize inexpensive, readily available grades of silica. Additionally, steam treatment of catalysts, with its high energy expenditure and risk of worker exposure, can be avoided with a room-temperature alcohol treatment.

DETAILED DESCRIPTION

Definitions

Certain terms as used in the present disclosure are defined in the following paragraphs as follows:

"Olefin" means an organic compound having one or more carbon-carbon double bonds. In particular examples, an olefin has the following formula:

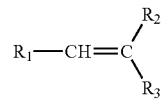

wherein $R_1$ is independently selected from hydrogen, a alkyl, a substituted or unsubstituted alkyl; $R_2$ is independently selected from hydrogen, a alkyl, a substituted or unsubstituted alkyl; and $R_3$ is independently selected from hydrogen, a alkyl, a substituted or unsubstituted alkyl.

"Peroxide" means a compound having one or more —O—OH functional groups and may include hydrogen peroxide ($H_2O_2$) and organic hydroperoxides (R—O—O—H, wherein R is a hydrocarbon or a functionalized hydrocarbon).

"Epoxide" means an organic compound having one or more three-membered rings in which two members of the ring are carbon and one is oxygen. More specifically, an epoxide has the following formula:

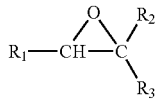

wherein $R_1$ is independently selected from hydrogen, a alkyl, a substituted or unsubstituted alkyl; $R_2$ is independently selected from hydrogen, a alkyl, a substituted or unsubstituted alkyl; and $R_3$ is independently selected from hydrogen, a alkyl, a substituted or unsubstituted alkyl.

For the purposes of all aspects of the present disclosure, an "alkyl" group is defined as a monovalent saturated hydrocarbon, which may be straight-chained or branched, or be or include cyclic groups. Non-limiting examples of alkyl groups are methyl, ethyl, n-propyl, i-propyl, n-butyl, i-butyl, t-butyl and n-pentyl groups. Preferably an alkyl group is straight-chained or branched and does not include any heteroatoms in its carbon skeleton. Preferably an alkyl group is a $C_1$-$C_{12}$ alkyl group, which is defined as an alkyl group containing from 1 to 12 carbon atoms. More preferably an alkyl group is a $C_1$-$C_6$ alkyl group, which is defined as an alkyl group containing from 1 to 6 carbon atoms. An alkyl group may also be a $C_1$-$C_4$ alkyl group, which is defined as an alkyl group containing from 1 to 4 carbon atoms.

For the purposes of this invention, a substituted group may be substituted monovalently with one or more of —F, —Cl, —Br, —I, —$CF_3$, —$CCl_3$, —$CBr_3$, —$CI_3$, —OH, —SH, —$NH_2$, —CN, —$NO_2$, and/or —COOH. Optional substituent(s) are not taken into account when calculating the total number of carbon atoms in the parent group substituted with the optional substituent(s). Preferably a substituted group comprises 1, 2 or 3 substituents, preferably 1 or 2 substituents, preferably 1 substituent.

"Mesoporous" means a material containing pores with diameters between 2 and 50 nm.

"Hydrocarbon" means an aliphatic, cycloaliphatic, or aromatic organic compound composed of only hydrogen and carbon.

"Hydrocarbon solvent" means an aliphatic, cycloaliphatic, or aromatic organic compound composed of only hydrogen and carbon that can be used as a solvent for washing an inorganic siliceous solid.

"Incipient wetness" means a technique in which a solid having a certain pore volume is impregnated with a volume of a solution less than or equal to the pore volume of the solid.

"Aromatic hydrocarbon" means an organic compound composed of only carbon and hydrogen having one or more benzene rings.

"$C_1$-$C_4$ alcohol" means a linear or branched aliphatic organic compound having from one to four carbon atoms and one hydroxyl group.

"Silylating agent" means a silicon compound capable of reaction with one or more hydroxyl groups of a composition to form at least one silicon-oxygen single bond.

"Silylated" means a composition in which one or more hydroxyl groups have been converted to silyl ethers through reaction with a silylating agent.

"Adiabatic" means a process in which heat is neither added nor intentionally removed from a system. In this context, adiabatic refers to using the heat of reaction of a siliceous solid with titanium tetrachloride as the principal or sole heat source in a catalyst preparation method.

Epoxidation

In general, epoxidation reactions may be represented by the following reaction scheme:

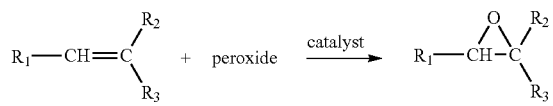

In epoxidation reactions, a mixture containing at least one olefin and a peroxide is contacted with a catalyst resulting in formation of the corresponding epoxide. In the above scheme, each of $R_1$, $R_2$, and $R_3$ are independently selected from hydrogen, alkyl, or substituted alkyl. When either of $R_1$, $R_2$, and $R_3$ are substituted, $R_1$, $R_2$, and $R_3$ contains one or more functional groups that are compatible with the peroxide and catalyst, such as hydroxyl or halide groups. In some embodiments, $R_1$, $R_2$, and $R_3$ are independently hydrogen or $C_1$-$C_{30}$ alkyl. In specific embodiments, $R_1$, $R_2$, and $R_3$ are independently hydrogen or $C_1$-$C_{10}$ alkyl.

Olefins suitable for use are well known and have at least one carbon-carbon double bond capable of epoxidation. Preferably, a $C_2$-$C_{60}$ olefin, more preferably a $C_3$-$C_{10}$ olefin, is used. Especially preferred olefins are acyclic $C_3$-$C_{10}$ olefins such as propylene, butene, pentene, hexene, heptene, octene, nonene, decene, and isomers thereof. Also preferred are olefins substituted with a hydroxyl or halogen such as allyl alcohol or allyl chloride.

Suitable organic peroxides are hydroperoxides that have the general structure R—OOH, where R is an aliphatic, cycloaliphatic, or aromatic radical, preferably with 3 to 50 carbons, more preferably 3 to 20 carbons. Preferred organic hydroperoxides are $C_3$-$C_{20}$ hydrocarbon hydroperoxides. Particularly preferred are $C_3$-$C_{15}$ secondary and tertiary hydroperoxides, for example, ethylbenzene hydroperoxide, tert-butylhydroperoxide, tert-amylhydroperoxide, cyclohexyl hydroperoxide, cumene hydroperoxide, and the like.

Hydrogen peroxide, an inorganic peroxide, is suitable for use in some olefin epoxidations as an alternative to organic hydroperoxides.

The olefin to peroxide or hydroperoxide molar ratio can vary, but it is preferable to use a molar ratio of from 1:1 to 20:1. A more preferred molar ratio of olefin to peroxide or hydroperoxide is 1.5:1 to 10:1.

The olefin to catalyst ratio can also vary. Generally, it is preferred to use the minimum concentration of catalyst effective to achieve a desirable epoxide yield and selectivity. In some embodiments, the catalyst to olefin ratio is within the range of 0.01 to 100 mmoles of titanium per mole of olefin; a more preferred range is from 0.1 to 10 mmoles of titanium per mole of olefin.

Catalyst

Catalysts useful for the present disclosure generally comprise titanium and a siliceous solid. In some embodiments, titanium is present in the catalyst in an amount (based upon the total weight of the catalyst) within the range of 0.5 to 10 wt. %, preferably 1 to 6 wt. %, more preferably 3 to 5 wt. %, based on the total weight of the catalyst. The source of titanium can vary and may be titanium halides, titanium alkoxides, titanium esters, or the like. Titanium halides are preferred, particularly titanium tetrachloride.

In addition to titanium, the catalysts comprise a siliceous solid. In some embodiments, the siliceous solid is present in the catalyst in an amount (based upon the total weight of the catalyst) within the range of 90 to 99.5 wt. %, preferably 94 to 99 wt. %, most preferably 95 to 97 wt. %, based on the total weight of the catalyst.

Catalysts useful for the present disclosure comprise a siliceous solid. Inorganic siliceous solids suitable for use are generally well known. The solids contain a major proportion of silicon dioxide ($SiO_2$) and may be referred to herein generically as "silicas." Amorphous (i.e., non-crystalline) silicon oxides are preferred.

Suitable inorganic siliceous solids include synthetic porous silicas, silica powders, refractory oxides, mesoporous molecular sieves, essentially pure silica, and other siliceous solids.

Suitable synthetic porous silicas consist of particles of amorphous silica flocculated or linked together so that the particles form a relatively dense, close-packed mass. Representatives of such materials are silica gel and precipitated silica. These silica products have numerous pores, voids, or interstices throughout their structures.

Suitable silica powders may include synthetic silica powders consisting of particles of amorphous silica flocculated in open-packed, readily disintegrated, loosely knit aggregates. Illustrative silica powders include fumed, pyrogenic silicas obtained by the combustion of hydrogen and oxygen with silicon tetrachloride or silicon tetrafluoride.

Refractory oxides are also suitable for use. These synthetic inorganic oxide materials contain a major proportion of silica. Suitable refractory oxides include silica-aluminas, silica-magnesias, silica-zirconias, silica-alumina-borias, silica-alumina-magnesias, and the like.

Molecular sieves, particularly large pore or mesoporous molecular sieves such as MCM-41, MCM-48 and M41S, may also be utilized as the inorganic siliceous solid.

Particularly preferred synthetic inorganic siliceous solids comprise essentially pure silica. "Essentially pure" silica as defined herein is at least 97 wt. % silica. Preferred essentially pure silicas may contain at least 98 wt. % silica, preferably at least 99 wt. % silica. Many silicas are commercially available and sold for various purposes, such as thin layer chromatography, column chromatography, catalyst supports, and other uses. Suitable silicas include, for example, Davisil® silica gels such as Davisil® 643 (products of Grace Davison) and microspherical silica gels produced by PQ Corporation in the "MS-" series, including MS-3050 silica, a grade commonly used to support polyolefin catalysts.

Other siliceous inorganic solids include naturally occurring mineral silicates such as hydrous magnesium silicates, and clay minerals such as hectorites, kaolins, bentonites, and the like.

Suitable inorganic siliceous solids have a pore volume of at least 0.8 $cm^3/g$, more preferably at least 1 $cm^3/g$, even more preferably at least 2 $cm^3/g$, and most preferably at least 3 $cm^3/g$. In some embodiments, the siliceous solid has a pore volume ranging from 0.8 $cm^3/g$ to 5 $cm^3/g$. In some embodiments, the siliceous solid has a pore volume ranging from 1.0 $cm^3/g$ to 4.5 $cm^3/g$. In some embodiments, the siliceous solid has a pore volume ranging from 2.0 $cm^3/g$ to 5 $cm^3/g$. In some embodiments, the siliceous solid has a pore volume ranging from 3.0 $cm^3/g$ to 5 $cm^3/g$. In some embodiments, the siliceous solid has a pore volume ranging from 3.0 $cm^3/g$ to 4.5 $cm^3/g$. In some embodiments, the siliceous solid has a pore volume ranging of 3.2 $cm^3/g$.

Preferred siliceous solids have high surface areas, particularly at least 25 $m^2/g$, preferably at least 200 $m^2/g$, more preferably at least 400 $m^2/g$, and most preferably at least 500 $m^2/g$. A preferred range is from 25 to 1000 $m^2/g$, more preferably from 200 to 1000 $m^2/g$.

In some embodiments, the physical form of catalyst includes, but is not limited to, powder, flakes, granules, spheres, or pellets. The inorganic siliceous solid may be in such form prior to impregnation and calcination or, alternatively, be converted after impregnation and/or calcination from one form to a different physical form by conventional techniques such as extrusion, pelletization, grinding, or the like.

In some embodiments, the catalyst may be reacted with a silylating agent. Generally, the amount of silylating agent used is an amount effective to reduce the concentration of surface hydroxyl groups on the siliceous solid and convert at least some of those groups to silyl ethers. In some embodiments, the amount of silylating agent used will be within the range of 10 to 70 wt. %, preferably 20 to 50 wt. %, based on the total amount of catalyst. In other embodiments, the amount of silylating agent used will be within the range of 0.2 to 2 moles, preferably 0.5 to 1.5 moles, per mole of free hydroxyl groups present in the siliceous solid.

Suitable silylating agents are silicon compounds capable of reaction with one or more hydroxyl groups of a composition, usually a siliceous solid, to form at least one silicon-oxygen single bond. Suitable silylating agents include, for example, organosilanes, organosilylamines and organosilazanes. Suitable organosilanes include, for example, chlorotrimethylsilane, dichlorodimethylsilane, chlorotriethylsilane, chlorodimethylphenylsilane, and the like. Preferred silylating agents include tetra-substituted silanes having from 1 to 3 halo substituents selected from chlorine, bromine, and iodine with the remainder of the substituents being methyl, ethyl or a combination thereof. Suitable organodisilazanes may have the formula:

$$R_3Si-NH-Si-R_3$$

wherein each R is independently a alkyl group (preferably, $C_1$-$C_4$ alkyl) or hydrogen. Especially preferred are hexaalkyl-substituted disilazanes such as, for example, hexamethyidisilazane.

In one aspect, the present disclosure relates to a method of preparing a catalyst. In some embodiments, the catalyst may be used for an olefin epoxidation reaction. In general, the method for making the catalyst includes three steps. In a first step, an inorganic siliceous solid is added to a column to produce a solid-filled column. In a second step, a solution comprising titanium tetrachloride and a hydrocarbon solvent is added to the solid-filled column to produce a titanium tetrachloride-impregnated solid. In a third step, the titanium tetrachloride-impregnated solid is calcined to produce the catalyst.

In some embodiments, the method for making the catalyst includes a step in which the titanium tetrachloride-impregnated solid is washed with a hydrocarbon solvent. Thus, in a first step, an inorganic siliceous solid is added to a column to produce a solid-filled column. In a second step, a solution comprising titanium tetrachloride and a hydrocarbon solvent is added to the solid-filled column to produce a titanium tetrachloride-impregnated solid. In a third step, the titanium tetrachloride-impregnated solid is washed with a hydrocarbon solvent to produce a washed titanium tetrachloride-impregnated solid. In a fourth step, the washed titanium tetrachloride-impregnated solid is calcined to produce the catalyst.

In other embodiments, the method for making the catalyst includes a step in which a calcined, titanium tetrachloride-impregnated solid is washed with a $C_1$-$C_4$ alcohol. Thus, in a first step, an inorganic siliceous solid is added to a column to produce a solid-filled column. In a second step, a solution comprising titanium tetrachloride and a hydrocarbon solvent is added to the solid-filled column to produce a titanium tetrachloride-impregnated solid. In a third step, the titanium tetrachloride-impregnated solid is calcined to produce a calcined solid. In a fourth step, the calcined solid is washed, preferably at room temperature, with a $C_1$-$C_4$ alcohol to produce an alcohol-washed catalyst.

In specific embodiments, the method for making the catalyst includes both a hydrocarbon washing step and an alcohol washing step. Thus, in a first step, an inorganic siliceous solid is added to a column to produce a solid-filled column. In a second step, a solution comprising titanium tetrachloride and a hydrocarbon solvent is added to the solid-filled column to produce a titanium tetrachloride-impregnated solid. In a third step, the titanium tetrachloride-impregnated solid is washed with a hydrocarbon solvent to produce a washed titanium tetrachloride-impregnated solid. In a fourth step, the washed titanium tetrachloride-impregnated solid is calcined to produce a calcined solid. In a fifth step, the calcined solid is washed, preferably at room temperature, with a $C_1$-$C_4$ alcohol to produce an alcohol-washed catalyst.

In some embodiments, the method for making the catalyst includes treatment with a silylating agent to produce a silylated catalyst.

In a specific embodiment, the method for making the catalyst involves four steps. In a first step, an inorganic siliceous solid is added to a column to produce a solid-filled column. In a second step, a solution comprising titanium tetrachloride and a hydrocarbon solvent is added to the solid-filled column to produce a titanium tetrachloride-impregnated solid. In a third step, the titanium tetrachloride-impregnated solid is calcined to produce a calcined solid. In a fourth step, the calcined solid is reacted with a silylating agent to produce a silylated catalyst.

In another specific embodiment, a hydrocarbon washing step is included. Thus, in a first step, an inorganic siliceous solid is added to a column to produce a solid-filled column. In a second step, a solution comprising titanium tetrachloride and a hydrocarbon solvent is added to the solid-filled column to produce a titanium tetrachloride-impregnated solid. In a third step, the titanium tetrachloride-impregnated solid is washed with a hydrocarbon solvent to produce a washed titanium tetrachloride-impregnated solid. In a fourth step, the washed titanium tetrachloride-impregnated solid is calcined to produce a calcined solid. In a fifth step, the calcined solid is reacted with a silylating agent to produce a silylated catalyst.

In another specific embodiment, an alcohol washing step is included. Thus, in a first step, an inorganic siliceous solid is added to a column to produce a solid-filled column. In a second step, a solution comprising titanium tetrachloride and a hydrocarbon solvent is added to the solid-filled column to produce a titanium tetrachloride-impregnated solid. In a third step, the titanium tetrachloride-impregnated solid is calcined to produce a calcined solid. In a fourth step, the calcined solid is washed, preferably at room temperature, with a $C_1$-$C_4$ alcohol to produce an alcohol-washed solid. In a fifth step, the alcohol-washed solid is reacted with a silylating agent to produce a silylated catalyst.

In yet another specific embodiment, hydrocarbon and washing steps are included. Thus, in a first step, an inorganic siliceous solid is added to a column to produce a solid-filled column. In a second step, a solution comprising titanium tetrachloride and a hydrocarbon solvent is added to the solid-filled column to produce a titanium tetrachloride-impregnated solid. In a third step, the titanium tetrachloride-impregnated solid is washed with a hydrocarbon solvent to produce a washed titanium tetrachloride-impregnated solid. In a fourth step, the washed titanium tetrachloride-impregnated solid is calcined to produce a calcined solid. In a fifth step, the calcined solid is washed, preferably at room temperature, with a $C_1$-$C_4$ alcohol to produce an alcohol-washed solid. In a sixth step, the alcohol-washed solid is reacted with a silylating agent to produce a silylated catalyst.

In embodiments of the present disclosure, an inorganic siliceous solid is added to a column. Suitable columns include, but are not limited to columns that may be used for chromatography. Although the column may be made of a variety of materials, the column should be acid-resistant because HCl is generated, in situ, when the siliceous solid is contacted with the titanium tetrachloride solution. Additionally, the column should be temperature resistant due to high calcination temperatures. For example, quartz columns are preferred, especially for small-scale laboratory preparations. Suitable columns may have a cylindrical shape.

The addition can be done in any desired manner, and the amount of siliceous solid used can vary. In some embodiments, it is possible to fill only a minor proportion of the column, or most of it, as the circumstances may suggest. For instance, the column may be filled with siliceous solid to a column height that exceeds the inside diameter of the column, although this need not be the case. It may be desirable, in some cases, to use a filter funnel or similar device as a substitute for the column, in which case, the diameter of the silica column will often exceed its height. Upon addition of the siliceous solid to the column, a solid-filled column is produced.

The inorganic siliceous solid may be dried, if desired, before or after it is added to the column. Drying may be accomplished, for example, by heating the inorganic siliceous solid for several hours at a temperature from 100° C. to 700° C., preferably 200° C. to 600° C. Vacuum or a flowing stream of a dry gas such as nitrogen may be applied to accelerate drying.

In embodiments of the present disclosure, after adding the siliceous solid to the column, a solution comprising titanium tetrachloride and a hydrocarbon solvent is added to the solid-filled column. This produces a titanium tetrachloride-impregnated solid. The $TiCl_4$ solution and siliceous solid are preferably combined under an inert atmosphere such as nitrogen, argon, helium, or the like, preferably nitrogen.

Any desired source of titanium tetrachloride can be used, and a variety of hydrocarbon solvents might be most suitable for the intended use. A "custom" solution can be made, for instance, by combining enough neat titanium tetrachloride with the desired hydrocarbon to give a solution of the required $TiCl_4$ concentration. In some examples, hydrocarbon solutions of 1 M $TiCl_4$ in toluene or hexanes may be used. Suitable hydrocarbons include, for example, $C_4$-$C_{30}$ alkyl, aliphatic, cycloaliphatic, and aromatic hydrocarbons. Aromatic hydrocarbons such as toluene or xylenes, especially toluene, are particularly preferred. The titanium tetrachloride solution is generally applied to the column of siliceous solid in a manner effective to control the temperature within the column. The resulting product is a titanium tetrachloride-impregnated solid.

Use of a column and the titanium tetrachloride solution, particularly the commercially available 1 M solutions, allows great precision in delivering a specific amount of titanium tetrachloride at a controlled pace. The level of precision offered by the method of the present disclosure is difficult to achieve when using other methods for treating the silica with titanium tetrachloride, particularly the gas-phase treatment of silica with titanium tetrachloride.

In some embodiments of the present disclosure, adiabatic temperature changes that occur when the $TiCl_4$ solution is applied to the siliceous solid in the column are controlled by adjusting the concentration of titanium tetrachloride in the solution, the rate of addition of the solution to the column, or both. The column temperature at one or multiple points is easily monitored using thermocouples or similar means to inform a decision about whether the rate of addition of $TiCl_4$ is too slow, too fast, or is proceeding at the desired rate. Consequently, process controls can be implemented if desired to automate delivery of the $TiCl_4$ solution to the column.

In some embodiments, following addition of the titanium chloride solution to the column and prior to any calcination, additional hydrocarbon solvent may be used to wash the titanium tetrachloride-impregnated solid. The resulting product is a washed titanium tetrachloride-impregnated solid. Preferably, this solvent is the same as the one used for the $TiCl_4$ solution. Preferably, a toluene or hexane solution of $TiCl_4$ is used, and additional toluene or hexane is used to wash the titanium tetrachloride-impregnated solid. Toluene is most preferred as the $TiCl_4$ solvent and as the wash solvent. The amount of hydrocarbon used to wash the titanium tetrachloride-impregnated solid can vary and is left to the skilled person's discretion. In specific embodiments, enough hydrocarbon solvent is used to remove residual $TiCl_4$ reagent. Preferably, the wash solvent is recovered by distillation or other means and is reused as a wash solvent. The wash step is preferably performed in the column and at room temperature.

The elution rate of hydrocarbon solvent through the column can be controlled by any desired means. In some embodiments, the grade of siliceous solid is chosen to optimize the flow rate of the hydrocarbon solvent. In specific embodiments, the flow rate is adjusted to be efficient while providing thorough washing with a minimum of hydrocarbon solvent. Generally, the wash step will be complete within minutes rather than hours.

Hydrocarbon washing may be helpful for removing excess titanium tetrachloride from the column, i.e., titanium tetrachloride that has not reacted with the siliceous solid, as well as other by-products such as hydrogen chloride.

In some embodiments, the titanium tetrachloride-impregnated solid, with or without the washing step described in the preceding paragraph, may be calcined at a temperature from 500° C. to 1000° C. to produce a calcined solid or catalyst. The calcination is preferably performed in an inert atmosphere such as nitrogen, argon, helium, or the like, preferably nitrogen. Preferably, calcination is performed at a temperature from 500° C. to 750° C., more preferably from 600° C. to 700° C. It is convenient, although not necessary, to perform the calcination in the same column used to prepare the titanium tetrachloride-impregnated solid. Calcination is generally performed for 0.1 to 24 hours, or for 1 to 18 hours, or for 1 to 4 hours.

Calcined solids or catalysts may be more effective in achieving a high conversion of olefin to epoxide, a high epoxide selectivity, or both.

In some embodiments of the present disclosure, the catalyst may be washed with a $C_1$-$C_4$ alcohol following calcination to produce an alcohol-washed catalyst. Suitable $C_1$-$C_4$ alcohols include, for example, methanol, ethanol, isopropyl alcohol, isobutyl alcohol, n-butyl alcohol, sec-butyl alcohol, tert-butyl alcohol, and the like. Methanol and ethanol are preferred. Methanol is most preferred. Solutions of $C_1$-$C_4$ alcohols and water can also be used. For example, a 9:1 solution of methanol and water is effective (see Table 7 below). The wash step is preferably performed in the column and at room temperature.

The elution rate of the $C_1$-$C_4$ alcohol through the column can be controlled by any desired means. In some embodiments, the grade of siliceous solid is chosen to optimize the flow rate of the $C_1$-$C_4$ alcohol. In specific embodiments, the flow rate is adjusted to be efficient while providing thorough washing with a minimum of $C_1$-$C_4$ alcohol. Generally, the $C_1$-$C_4$ alcohol wash step will be complete within minutes rather than hours.

Surprisingly, it was found that alcohol washing overcomes any need to steam treat a catalyst following calcination. Although steam treatment has been commonly used to reduce chloride content, it is preferably avoided because of the energy costs and challenges in handling hot condensate, including potential worker exposure. The amount of $C_1$-$C_4$ alcohol (if any) used to wash the catalyst can vary and is left to the skilled person's discretion. In specific embodiments, enough $C_1$-$C_4$ alcohol is used to remove residual chloride ions present. Preferably, the $C_1$-$C_4$ alcohol is recovered by distillation or other means and is reused as a wash solvent.

In some embodiments, the catalyst may be reacted with a silylating agent to produce a silylated catalyst, which may improve epoxide selectivity. Generally, the amount of silylating agent used is an amount effective to reduce the concentration of surface hydroxyl groups on the siliceous solid and convert at least some of those groups to silyl ethers. Silylation is optionally used following calcination and any alcohol washing step. Treatment with the silylating agent may be performed either in the liquid phase (i.e., where the silylating agent is applied to the catalyst as a liquid, either by itself or as a solution in a suitable solvent such as a hydrocarbon) or in the vapor phase (i.e., where the silylating agent is contacted with the catalyst in the form of a gas). Treatment temperatures are preferably from 80° C. to 450° C., with somewhat higher temperatures (e.g., 300° C. to 425° C.) preferred when the silylating agent is an organohalosilane and somewhat lower temperatures (e.g., 80° C. to 300° C.) preferred for the organosilazanes.

The present disclosure provides a process for forming an epoxide. The process comprises contacting a solution of an olefin, preferably propylene, and a peroxide with a catalyst to produce the epoxide. The catalyst, which has already been discussed in detail above, is made by a method comprising adding an inorganic siliceous solid to a column to produce a solid-filled column, adding to the solid-filled column a solution comprising titanium tetrachloride and a hydrocarbon solvent to produce a titanium tetrachloride-impregnated solid, and calcining the titanium tetrachloride-impregnated solid at a temperature from 500° C. to 1000° C. to produce the catalyst. The inorganic siliceous solid has a pore volume of at least 0.8 $cm^3$/g.

Generally, epoxidation is conducted in the liquid phase in solvents or diluents that are liquid at the reaction temperature and pressure and are substantially inert to the reactants and the products produced therefrom. In commercial practice, it is generally most economical to use as a solvent the hydrocarbon or alcohol used to produce the organic hydroperoxide reactant. For example, when tert-butylhydroperoxide is utilized, tert-butyl alcohol is preferred as the epoxidation solvent.

In some embodiments, the peroxide is selected from the group consisting of hydrogen peroxide and organic hydroperoxides. Preferably, the organic hydroperoxide is selected from the group consisting of tert-butylhydroperoxide and ethylbenzene hydroperoxide. The organic hydroperoxide may be present at concentrations of from about 1 to 50 wt. % of the epoxidation reaction mixture (including olefin).

Epoxidation may be conducted at moderate temperatures and pressures. Suitable reaction temperatures vary from 0° C. to 200° C., but preferably from 25° C. to 150° C. The reaction is preferably conducted at or above atmospheric pressure. The pressure may vary from 1 atmosphere to 100 atmospheres. The reaction mixture may, for example, be maintained substantially in a non-gaseous phase or as a two-phase (gas/liquid) system. The catalyst, of course, is heterogeneous and thus is present as a solid phase during the epoxidation process.

Suitable reactor configurations for epoxidation include, but are not limited to continuous, batch, or semi-continuous procedures. When the epoxidation has proceeded to the desired extent, the product mixture is separated and the products (epoxide and the alcohol derived from the organic hydroperoxide) are recovered by conventional methods such as fractional distillation, selective extraction, filtration, and the like. The reaction solvent, the catalyst composition, and any unreacted olefin or organic hydroperoxide may be recycled and reused.

The epoxidation reaction provides an epoxide product in accord with the following reaction scheme:

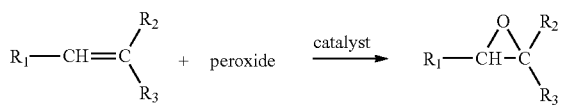

Suitable epoxide products have the formula shown above in which each of $R_1$, $R_2$, and $R_3$ is independently hydrogen, alkyl, or alkyl substituted with one or more functional groups that are compatible with the peroxide and catalyst, such as hydroxyl or halide groups. In some embodiments, $R_1$, $R_2$, and $R_3$ are independently hydrogen or $C_1$-$C_{30}$ alkyl. In specific embodiments, $R_1$, $R_2$, and $R_3$ are independently hydrogen or $C_1$-$C_{10}$ alkyl.

The epoxide may derive from epoxidation of a $C_2$-$C_{60}$ olefin, more preferably a $C_3$-$C_{10}$ olefin. Especially preferred epoxides result from epoxidation of acyclic $C_3$-$C_{10}$ olefins to give epoxides such as propylene oxide, 1,2-butene oxide, isobutylene oxide, pentene oxides, hexene oxides, heptane oxides, octane oxides, nonene oxides, decene oxides, and the like. Also preferred are epoxides substituted with a hydroxyl or halogen such as glycidol and epichlorohydrin. Propylene oxide is most preferred.

In some embodiments, the peroxide conversion is at least 50%, preferably at least 60%, more preferably at least 70%, and most preferably at least 80%. A preferred range is 50 to 99%, preferably 60 to 99%, more preferably 70 to 99%. As shown in the examples below, peroxide conversion improves when the column preparation method of the present disclosure is used. The term "peroxide conversion," as used herein refers to the percentage of inorganic peroxide or organic hydroperoxide that is converted to water or an alcohol, respectively. Thus, for example, when TBHP is the peroxide, the percentage of TBHP molecules converted to tert-butyl alcohol is the "peroxide conversion."

In some embodiments, the peroxide selectivity is greater than 95%, preferably greater than 97%, more preferably greater than 98%. As shown in the examples below, peroxide selectivity improves when the column preparation method of the present disclosure is used. The term "peroxide selectivity," as used herein refers to the percentage of inorganic peroxide or organic hydroperoxide for which the active oxygen from the peroxide is incorporated into an epoxide product. Thus, for example, when TBHP is the peroxide, and propylene is the olefin, the percentage of active oxygens from the converted TBHP molecules that become incorporated into a propylene oxide molecule is the "peroxide selectivity."

Catalyst Preparation Examples

Silica Supports

Silica supports tested include MCM-41 mesoporous silica (Aldrich, surface area: 1000 m²/g, pore volume: 0.98 cm³/g), Davisil® 643 silica (product of Grace Davison, surface area: 300 m²/g, pore volume: 1.15 cm³/g), and MS-3050 silica (a commercially available product of PQ Corporation, surface area: 490 m²/g, pore volume: 3.2 cm³/g).

Column-Prepared Catalysts

Catalyst 1A: A sample of mesoporous silica ("MCM-41," 0.5 g) is charged to a small (⅜" ID) column and heated for 2 h at 200° C. After the column cools, a solution of titanium tetrachloride (0.5 mL of 1.0 M solution in toluene) is added slowly to the top of the column under a nitrogen atmosphere. When the TiCl₄ addition is complete, additional toluene (3.0 mL) is added to the top of the column to wash the resulting catalyst. The product is calcined for 2 h at 700° C. under a 100 mL/min nitrogen stream.

Catalyst 1B: The procedure used to make Catalyst 1A is repeated except that a 1.0 M solution of titanium tetrachloride in n-hexane is used (0.5 mL), and when the TiCl₄ addition is complete, additional n-hexane (3.0 mL) is used to wash the catalyst. The product is calcined for 2 h at 700° C. under a 100 mL/min nitrogen stream.

Catalyst 2A: The procedure used to make Catalyst 1A is repeated except that Davisil® 643 silica (0.50 g, calcined 2 h at 200° C.) is used instead of MCM-41, and the amount of 1.0 M titanium tetrachloride/toluene used is 1.5 mL. The product is calcined for 2 h at 700° C. under a 100 mL/min nitrogen stream.

Catalyst 3A (includes methanol washing): A sample of MCM-41 silica (3.77 g) is charged to a small (½" ID) column and heated for 2 h at 200° C. After the column cools, a solution of titanium tetrachloride (7.5 mL of 1.0 M solution in toluene) is added slowly to the top of the column. When the TiCl₄ addition is complete, additional toluene (23 mL) is added to the top of the column to wash the resulting catalyst. The product is calcined for 2 h at 700° C. under a 100 mL/min nitrogen stream. Thereafter, the catalyst is washed with methanol (40 mL) and dried for 2 h at 200° C. The dried product, still in the column, is treated with hexamethyldisilazane ("HMDS," 1.2 mL) and heated at 170° C. for 0.5 h under a 100 mL/min nitrogen stream.

Catalyst 3B (includes methanol washing): The procedure used to make Catalyst 3A is modified as follows. MCM-41 silica (0.509 g) that has been calcined overnight at 200° C.

is used. A solution of titanium tetrachloride (1.0 mL of 1.0 M solution in toluene) is added slowly to the top of the column. When the TiCl₄ addition is complete, additional toluene (3.0 mL) is added to the top of the column to wash the resulting catalyst. The product is calcined for 2 h at 700° C. under a 100 mL/min nitrogen stream. Thereafter, the catalyst is washed with methanol (10 mL) and dried for 2 h at 200° C. The dried product, still in the column, is treated with HMDS (0.3 mL) and heated at 170° C. for 0.5 h under a 100 mL/min nitrogen stream.

Catalyst 4A (includes methanol washing): A sample of MS-3050 silica (2.01 g) is charged to a small (½" ID) column and heated for 2 h at 200° C. After the column cools, a solution of titanium tetrachloride (4.0 mL of 1.0 M solution in toluene) is added slowly to the top of the column. When the TiCl₄ addition is complete, additional toluene (12 mL) is added to the top of the column to wash the resulting catalyst. The product is calcined for 2 h at 700° C. under a 100 mL/min nitrogen stream. Thereafter, the catalyst is washed with methanol (40 mL) and dried for 2 h at 200° C. The dried product, still in the column, is treated with HMDS (1.2 mL) and heated at 170° C. for 0.5 h under a 100 mL/min nitrogen stream.

Comparative Catalysts

Catalyst 1C: A sample of MCM-41 silica (2.02 g) is calcined for 2 h at 200° C. in a column. Neat titanium tetrachloride (0.57 mL) is applied to a quartz wool plug inserted into the top of the column. The plug is heated to 200° C. in a stream of nitrogen (100 mL/min) to generate a flow of TiCl₄ vapor that passes through the column. Thereafter, the catalyst is calcined for 2 h at 700° C. under a 100 mL/min nitrogen stream.

Catalyst 1D: MCM-41 silica is calcined for 2 h at 250° C. A sample of the calcined silica (0.50 g) is placed in a round-bottom flask. Titanium tetrachloride (0.80 mL of 1.0 M solution in toluene) is added to the silica to form a wet cake. The mixture is allowed to react for 2 days. Thereafter, the catalyst is calcined for 4 h at 700° C. under nitrogen.

Catalyst 2B: Davisil® silica is calcined for 2 h at 250° C. A sample of the calcined silica (0.50 g) is placed in a round-bottom flask. Titanium tetrachloride (0.70 mL of 1.0 M solution in toluene) is added to the silica and mixed to form a free-flowing powder. The mixture is allowed to react for 2 days. Thereafter, the catalyst is calcined for 4 h at 700° C. under nitrogen.

Catalyst 2C: Davisil® silica is calcined for 2 h at 250° C. A sample of the calcined silica (0.30 g) is placed in a round-bottom flask and is slurried with toluene (3.0 mL). Titanium tetrachloride (0.50 mL of 1.0 M solution in toluene) is added to the suspension. The mixture is stirred for 0.5 h, and is then filtered. The solids are washed with more toluene (3 mL), and the resulting catalyst is calcined for 4 h at 700° C. under nitrogen.

Catalyst 3C (includes steam treatment): A sample of MCM-41 silica (2.0 g) is charged to a small (½" ID) column and heated overnight at 200° C. After the column cools, a solution of titanium tetrachloride (4.0 mL of 1.0 M solution in toluene) is added slowly to the top of the column. When the TiCl₄ addition is complete, additional toluene (3.0 mL) is added to the top of the column to wash the resulting catalyst. The product is calcined for 2 h at 700° C. under a 100 mL/min nitrogen stream. Thereafter, the catalyst is steam treated (3.0 mL of H₂O) at 400° C. The product, still in the column, is treated with HMDS (1.2 mL) and heated at 170° C. for 0.5 h under a 100 mL/min nitrogen stream.

Batch epoxidation of 1-octene using TBHP oxidate

An aliquot (14 mL) of a 1-octene solution of 41% tert-butylhydroperoxide (TBHP) in tert-butyl alcohol (4.4 wt. % TBHP in 1-octene) is placed in a round-bottom flask equipped with a magnetic stir bar. The mixture is heated to 80° C. under nitrogen. The epoxidation reaction is started by adding a catalyst sample of specified weight (see Tables 1-4). The reaction continues for 1 h, after which a sample is removed from the flask using a needle with an in-line filter. TBHP content before and after the test is determined by iodometric titration, and the % conversion is calculated. Results appear in Tables 1-4.

TABLE 1

Effect of Column Preparation (MCM-41 silica)

| Catalyst | Amount, g | Preparation method | TBHP conversion, % |
|---|---|---|---|
| 1A | 0.046 | column (toluene) | 55.8 |
| 1B | 0.048 | column (hexane) | 51.4 |
| 1C* | 0.056 | vapor-phase addition of TiCl₄ | 45.1 |
| 1D* | 0.109 | incipient wetness, 2-day reaction | 10.2 |

*Comparative examples

Table 1 summarizes results with MCM-41, a mesoporous silica. Column preparation of the catalyst provides improved TBHP conversion when compared with either preparation by treatment of the silica with gas-phase TiCl₄ (Catalyst 1C) or preparation by incipient wetness (Catalyst 1D). Interestingly, there is a further significant improvement when an aromatic hydrocarbon (toluene) is used instead of an aliphatic hydrocarbon (hexane) as the solvent for the TiCl₄ and as the wash solvent.

TABLE 2

Effect of Column Preparation (Davisil® 643 silica)

| Catalyst | Amount, g | Preparation method | TBHP conversion, % |
|---|---|---|---|
| 2A | 0.057 | column (toluene) | 46.6 |
| 2B* | 0.109 | incipient wetness, 2-day reaction | 44.2 |
| 2C* | 0.108 | slurry | 48.6 |

*Comparative example

Table 2 shows a similar improvement from use of the column preparation technique when Davisil® 643 silica, a readily available and inexpensive silica grade, is used instead of MCM-41. Note that Catalysts 2B and 2C require almost double the amount of catalyst to get a similar TBHP conversion to that of Catalyst 2A.

TABLE 3

Effect of Methanol Wash (MCM-41 silica)

| Catalyst | Amount, g | Preparation method | TBHP conversion, % |
|---|---|---|---|
| 3A | 0.056 | column (toluene), MeOH wash, HMDS | 70.5 |
| 3B | 0.050 | column (toluene), MeOH wash, HMDS | 68.1 |
| 3C* | 0.055 | column (toluene), steam treat, HMDS | 67.7 |

*Comparative example

Although it was previously believed that steam treatment of titanated silicas was needed to remove remaining chloride on the catalyst after the TiCl₄ reacts with surface hydroxyls on the silica (see Catalysis Today 93-95 (2004) at p. 202), it was surprisingly found that a wash step with methanol at room temperature can eliminate the need for steam treatment. Table 3 shows that high TBHP conversion can be maintained while avoiding the more challenging and energy-intensive steam treatment.

TABLE 4

Effect of Silica Surface Area and Pore Volume

| Catalyst | Amount, g | | TBHP conversion, % |
|---|---|---|---|
| | | Preparation method: column | |
| 1A | 0.046 | MCM-41: SA = 1000 m$^2$/g, PV = 0.98 cm$^3$/g | 55.8 |
| 2A* | 0.057 | Davisil ® 643: SA = 300 m$^2$/g, PV = 1.15 cm$^3$/g Preparation method: column, MeOH wash | 46.6 |
| 4A | 0.051 | MS-3050: SA = 490 m$^2$/g, PV = 3.2 cm$^3$/g | 67.5 |
| 3A* | 0.056 | MCM-41: SA = 1000 m$^2$/g, PV = 0.98 cm$^3$/g | 70.5 |

*Comparative example

Table 4 shows the impact of surface area and pore volume of the silica. When the column method of catalyst preparation is used, tripling the surface area from 300 to 1000 m$^2$/g (Catalyst 1A versus Catalyst 2A) provides a higher TBHP conversion with less catalyst. The impact of pore volume is demonstrated in the second pair of examples, where the pore volume is tripled from 0.98 cm$^3$/g to 3.2 cm$^3$/g. Here, although the surface area of MS-3050 is only half that of MCM-41, the greater pore volume compensates, resulting in a catalyst that is at least as effective in converting TBHP (taking into account normalized catalyst amounts). Importantly, however, MS-3050, a support that is widely used to support olefin polymerization catalysts, is inexpensive, readily available, durable, and can be obtained with high batch-to-batch consistency. Thus, MS-3050 and its analogs are an attractive alternative to MCM-41.

Continuous Propylene Epoxidation

A small, continuous unit is used to compare catalyst performance under the following conditions: pressure: 800 psig; temperature: 80° C.; propylene feed rate: 5 g/h (9.6 mL/h); TBHP feed rate: 8.55 g/h (10.0 mL/h); total volumetric flow: 19.6 mL/h; molar ratio of propylene to TBHP: 3.1. The catalysts tested are 4.5% Ti on MCM-41 silica (Aldrich) and 4.9% Ti on MS-3050 silica (PQ Corporation). Both catalysts are prepared by adding TiCl$_4$ (1M solution in toluene) to silica using the column treatment method described earlier. Results of continuous epoxidation after 100 h on stream are shown in Table 5.

TABLE 5

Results from Continuous Epoxidation of Propylene (100 h on stream)

| | Catalyst mass, g | Catalyst vol., mL | TBHP conv., % | TBHP->PO selectivity | PO prod., g/mL | km200 * 100 |
|---|---|---|---|---|---|---|
| 4.5% Ti on MCM-41 | 1.35 | 8.4 | 85.0 | 99.7 | 0.098 | 10.1 |
| 4.9% Ti on MS-3050 | 1.35 | 7.1 | 88.0 | 99.8 | 0.101 | 11.2 |

Column technique used to prepare both catalysts.

Table 5 shows that catalysts prepared using the column technique with either MCM-41 or MS-3050 silica provide good TBHP conversion and good propylene oxide productivity when tested in a continuous propylene epoxidation unit, and that the values remain favorable even after 100 hours on stream.

Additional Examples: Comparing Column vs. Incipient Wetness

The column technique is used generally as described above to prepare additional catalysts using the supports and experimental details identified in Table 6 (see examples with Catalysts 5A-5C). Comparative catalysts prepared by incipient wetness are also tested (Catalysts 5D-5L). Results for TBHP conversion and selectivity appear in the table.

TABLE 6

Column vs. Incipient Wetness Preparation Method

| Catalyst | Silica | Preparation Method | TBHP conv., % | TBHP select., % |
|---|---|---|---|---|
| 5A | D-643 | column; 0.3 g silica, 0.5 mL 1M TiCl$_4$ (tol.), wash with 3 mL toluene (4-5 wt. % Ti) | 65 | >95 |
| 5B | MCM-41 | column; 0.1 g silica, 0.5 mL 1M TiCl$_4$ (tol.), wash with 1 mL toluene (4-5 wt. % Ti) | 84 | >95 |
| 5C | MCM-41 | column; 0.1 g silica, 0.5 mL 1M TiCl$_4$ (tol.), wash with 3 mL toluene (4-5 wt. % Ti) | 88 | >95 |

TABLE 6-continued

Column vs. Incipient Wetness Preparation Method

| Catalyst | Silica | Preparation Method | TBHP conv., % | TBHP select., % |
|---|---|---|---|---|
| 5D* | D-643 | incipient wetness, 0.5 g silica, 0.7 mL 1M TiCl$_4$ (tol.), (6.3 wt. % Ti) | 44 | >95 |
| 5E* | D-643 | incipient wetness, 0.5 g silica, 0.4 mL 1M TiCl$_4$ (tol.), (3.7 wt. % Ti) | 44 | >95 |
| 5F* | D-643 | incipient wetness, 0.5 g silica, 0.2 mL 1M TiCl$_4$ (tol.), (1.9 wt. % Ti) | 30 | >95 |
| 5G* | D-643 | incipient wetness, 0.5 g silica, 0.1 mL 1M TiCl$_4$ (tol.), (0.95 wt. % Ti) | 38 | >95 |
| 5H* | MCM-41 | incipient wetness, 0.5 g silica, 0.7 mL 1M TiCl$_4$ (tol.), (6.3 wt. % Ti) | 36 | >95 |
| 5J* | MCM-41 | incipient wetness, 0.5 g silica, 0.4 mL 1M TiCl$_4$ (tol.), (3.7 wt. % Ti) | 34 | 92 |
| 5K* | MCM-41 | incipient wetness, 0.5 g silica, 0.2 mL 1M TiCl$_4$ (tol.), (1.9 wt. % Ti) | 39 | 91 |
| 5L* | MCM-41 | incipient wetness, 0.5 g silica, 0.1 mL 1M TiCl$_4$ (tol.), (0.95 wt. % Ti) | 36 | 88 |

*Comparative examples.

The examples in Table 6 demonstrate the superior results available from column preparation of titanated catalysts based on either MCM-41 or Davisil® 643 silica when compared with catalysts made by incipient wetness. None of the comparative catalysts (Catalysts 5D through 5L), which represent a range of Ti contents (0.95 to 6.3 wt. %), delivers the high TBHP conversions and selectivities observed with the column-prepared catalysts (Catalysts 5A-5C).

Additional Examples: Alcohol Wash vs. Steam Treatment

The column technique, with methanol washing at room temperature or steam treatment, is used to prepare additional catalysts using MCM-41. In general, the support is dried for 2 h at 200° C. in a vertical quartz tube under a nitrogen flow. The dry MCM-41 is treated with titanium tetrachloride (1 M solution in toluene, 2 mL/g) at room temperature in the same column and is then washed with toluene. The titanated support is then calcined for 2 h at 700° C. Thereafter, the catalyst is either washed with methanol (or a 9:1 MeOH/H$_2$O solution) at room temperature or is steamed at 400° C. The methanol-washed catalysts are calcined for 2 h at 200° C. Both catalyst types are treated with HMDS (0.6 mL/g) at 180° C. prior to testing. Results for catalyst activity and TBHP selectivity appear in Table 7.

TABLE 7

Effect of Alcohol Wash vs. Steam Treatment on Titanated MCM-41

| Cat. | Treatment | Wash/ support, mL/g | Activity, g TBHP/g cat/h | TBHP selectivity, % |
|---|---|---|---|---|
| 6A | MeOH wash, 25° C. | 20 | 6.17 | 100 |
| 6B | MeOH wash, 25° C. | 20 | 6.33 | 100$^a$ |
| 6C | MeOH wash, 25° C. | 15 | 5.70 | 99.8 |
| 6D | MeOH wash, 25° C. | 10 | 5.74 | 100$^b$ |
| 6E | MeOH:H$_2$O (9:1) wash, 25° C. | 20 | 5.77 | 100 |
| 6F* | Steam, 400° C. | 1.5 | 6.20 | 99.1 |
| 6G* | Steam, 400° C. | 1.5 | 6.46 | 97.1$^c$ |

*Comparative examples.
$^a$Repeat run with support dried overnight
$^b$Scaled up 4x
$^c$Catalyst exposed to air over the weekend.

Table 7 shows that alcohol washing is a desirable alternative to steam treatment at 400° C. High activities and high TBHP selectivities are achieved with methanol or aqueous methanol washing of the catalysts at room temperature.

We claim:

1. A method of preparing a catalyst, comprising:
   (a) adding an inorganic siliceous solid to a column to produce a solid-filled column;
   (b) adding to the solid-filled column a solution comprising titanium tetrachloride and a hydrocarbon solvent to produce a titanium tetrachloride-impregnated solid; and
   (c) calcining the titanium tetrachloride-impregnated solid at a temperature from 500-1000° C. under a nitrogen stream to produce the catalyst wherein the catalyst is prepared in the absence of steam.

2. The method of claim 1, wherein the titanium tetrachloride-impregnated solid from step (b) is washed with additional hydrocarbon solvent selected from toluene and hexane prior to calcination in step (c).

3. The method of claim 1, wherein the catalyst from step (c) is washed with a C$_1$-C$_4$ alcohol to produce an alcohol-washed catalyst.

4. The method of claim 3, wherein the alcohol-washed catalyst is reacted with a silylating agent to produce a silylated catalyst.

5. The method of claim 1, wherein the siliceous solid has a surface area from 25-1000 m$^2$/g.

6. The method of claim 1, wherein adiabatic temperature changes that occur in step (b) are controlled by adjusting the concentration of titanium tetrachloride in the solution, the rate of addition of the solution to the column, or both.

7. The method of claim 1, wherein the catalyst comprises from 0.5 to 10 wt. %, based on the amount of catalyst, of titanium.

8. A process for forming an epoxide, comprising contacting a solution of an olefin and a peroxide with a catalyst produced by the method of claim 1 to produce the epoxide.

9. The process of claim 8, wherein the olefin is propylene.

10. The process of claim 8, wherein the peroxide is selected from the group consisting of hydrogen peroxide and organic hydroperoxides.

11. The process of claim 10, wherein the organic hydroperoxide is selected from the group consisting of tert-butyl-hydroperoxide and ethylbenzene hydroperoxide.

12. The process of claim 8, wherein the peroxide conversion is at least 50%.

13. The process of claim 8, wherein peroxide selectivity is greater than 95%.

14. A method of preparing a catalyst, comprising:
(a) adding a mesoporous siliceous solid comprising a pore volume of 0.98-3.2 cm$^3$/g dried at a temperature of 200° C. for 2 hours to a column to produce a solid-filled column;
(b) adding to the solid-filled column a solution comprising titanium tetrachloride and a hydrocarbon solvent selected from toluene and hexane to produce a titanium tetrachloride-impregnated solid; and
(c) calcining the titanium tetrachloride-impregnated solid at a temperature from 600-700° C. for 2-4 hours under a 100 ml/min-nitrogen stream to produce the catalyst wherein the catalyst is prepared in the absence of steam.

15. The method of claim 3, wherein the $C_1$-$C_4$ alcohol is selected from methanol and ethanol.

16. The method of claim 1, wherein the inorganic siliceous solid has a pore volume of at least 0.8 cm$^3$/g.

* * * * *

UNITED STATES PATENT AND TRADEMARK OFFICE
CERTIFICATE OF CORRECTION

PATENT NO. : 9,433,925 B2  
APPLICATION NO. : 14/602410  
DATED : September 6, 2016  
INVENTOR(S) : Grey et al.

Page 1 of 1

It is certified that error appears in the above-identified patent and that said Letters Patent is hereby corrected as shown below:

In the Specification

| Column 14 | Line 36 | Delete "(Davisil ®)" and insert --(Davisil®)-- |
| Column 15 | Line 16 | Delete "Davisil ®" and insert --Davisil®-- |

In the Claims

| Column 18 | Line 34 | In Claim 1, delete "500-1000° C." and insert --500 °C.-1000 °C.-- |
| Column 19 | Line 13 | In Claim 14, delete "600-700° C." and insert --600 °C.-700 °C.-- |

Signed and Sealed this  
Twenty-second Day of January, 2019

Andrei Iancu  
*Director of the United States Patent and Trademark Office*